(12) United States Patent
Fisher

(10) Patent No.: US 7,834,207 B2
(45) Date of Patent: Nov. 16, 2010

(54) PERACETIC ACID IN AN ANHYDROUS STERILANT DELIVERY SYSTEM

(75) Inventor: Steven A. Fisher, Brookfield, IL (US)

(73) Assignee: American Air Liquide, Inc., Fremont, CA (US)

( * ) Notice: Subject to any disclaimer, the term of this patent is extended or adjusted under 35 U.S.C. 154(b) by 1159 days.

(21) Appl. No.: 11/456,804

(22) Filed: Jul. 11, 2006

(65) Prior Publication Data

US 2007/0073081 A1 Mar. 29, 2007

Related U.S. Application Data

(60) Provisional application No. 60/720,659, filed on Sep. 26, 2005.

(51) Int. Cl.
*C07C 409/44* (2006.01)

(52) U.S. Cl. ........................................... 562/1; 514/557

(58) Field of Classification Search ........................ None
See application file for complete search history.

(56) References Cited

U.S. PATENT DOCUMENTS

| | | | | |
|---|---|---|---|---|
| 5,567,444 A | * | 10/1996 | Hei et al. | 424/616 |
| 5,683,474 A | * | 11/1997 | Cotteret et al. | 8/409 |
| 5,977,045 A | * | 11/1999 | Murphy | 510/289 |
| 6,558,622 B1 | * | 5/2003 | Malchesky | 422/28 |
| 6,589,565 B1 | * | 7/2003 | Richter et al. | 424/616 |
| 6,593,283 B2 | * | 7/2003 | Hei et al. | 510/214 |
| 6,998,369 B2 | * | 2/2006 | Hei et al. | 510/111 |
| 7,108,832 B2 | * | 9/2006 | Christensen et al. | 422/28 |

OTHER PUBLICATIONS

"*Ozone/Chlorine Dioxide Oxidation Products of Organic Materials*", Proceedings of Conference held in Cincinnati, Ohio, Nov. 17-19, Rip G. Rice, et al. 1978, pp. 40-43, 48-49, and 54-55.

* cited by examiner

*Primary Examiner*—Daniel M Sullivan
*Assistant Examiner*—Chukwuma O Nwaonicha
(74) *Attorney, Agent, or Firm*—Christopher J. Cronin

(57) ABSTRACT

Method and system for forming an anhydrous sterilant. In one embodiment, anhydrous peracetic acid is combined with carbon dioxide, wherein the carbon dioxide is in one of a liquid, solid, and supercritical state.

4 Claims, 5 Drawing Sheets

PERACETIC ACID IN AN ANHYDROUS STERILANT DELIVERY SYSTEM

CROSS-REFERENCE TO RELATED APPLICATIONS

This application claims the benefit under 35 U.S.C. §119(e) to provisional application No. 60/720,659, filed Sep. 26, 2005, the entire contents of which are incorporated herein by reference.

BACKGROUND

Peracetic acid is effective in eliminating many kinds of harmful bacteria and molds and may be used for sterilization and sanitation of surfaces associated with food production and storage, such as aseptic packaging operations that bottle low-acid juices. In these applications, a hot aqueous solution of peracetic acid is sprayed on the inner surfaces of the bottles, which are then rinsed and dried. The peracetic acid is prepared by combining acetic acid with hydrogen peroxide in water. The hydrogen peroxide oxidizes the acetic acid in a reversible manner so that the resulting solution is an equilibrium mixture of hydrogen peroxide, acetic acid, and peracetic acid.

However, heating the peracetic acid solution and rinsing and drying sterilized surfaces require large amounts of energy, ventilation and time. Therefore, there exists a need for alternative approaches to treating surfaces with peracetic acid.

SUMMARY

The embodiments of the present invention generally provide a method and system for forming carbon dioxide sterilants. One embodiment of the invention provides a method for forming an anhydrous sterilant by combining anhydrous peracetic acid with carbon dioxide. The carbon dioxide may be in a liquid, solid, or supercritical state. The peracetic acid may be formed by oxidizing an anhydrous organic compound, such as anhydrous ethanol, anhydrous acetaldehyde, and anhydrous acetic acid, with ozone. In one embodiment, the anhydrous organic compound may be acetic acid. The ozone may be generated in a flow of gas having about 90% v/v or above oxygen, and the flow of gas may have a flow rate of between about 100 ml/min. and about 10000 ml/min. In another embodiment, the flow rate is between about 250 ml/min. and about 750 ml/min. The ozone may be ozone present in the flow of oxygen gas at a concentration between about 1% v/v and about 15% v/v. In the embodiments with liquid carbon dioxide, the liquid carbon dioxide may be maintained at a pressure of between about 100 PSI and about 900 PSI. The liquid carbon dioxide having peracetic acid may be released to a pressure of about 75 PSI or less (the triple point pressure) to form carbon dioxide snow having peracetic acid. The carbon dioxide snow may be compacted into dry ice wafers, cylinders, or bricks. In one embodiment, the anhydrous peracetic acid is present in the carbon dioxide at a concentration between about 0.05 mole % and about 15 mole %.

Another embodiment of the invention provides a method for forming an anhydrous sterilant by contacting ozone with an anhydrous organic compound in a reaction vessel to form anhydrous peracetic acid, and, combining the anhydrous peracetic acid with carbon dioxide. The carbon dioxide may be in a liquid, solid, or supercritical state. The anhydrous organic compound may be selected from the group consisting of anhydrous ethanol, anhydrous acetaldehyde, and anhydrous acetic acid. In one embodiment, the anhydrous organic compound is acetic acid. In the embodiments with liquid carbon dioxide, the liquid carbon dioxide may be maintained at a pressure of between about 100 PSI and about 900 PSI. The liquid carbon dioxide having peracetic acid may be released to a pressure of about 75 PSI or less to form carbon dioxide snow having peracetic acid. The carbon dioxide snow may be compacted into dry ice wafers, cylinders, or bricks. In one embodiment, the anhydrous peracetic acid is present in the carbon dioxide at a concentration between about 0.05 mole % and about 15 mole %.

Another embodiment of the invention provides a method for forming an anhydrous sterilant by introducing an anhydrous organic compound into liquid carbon dioxide or supercritical carbon dioxide; and contacting ozone with the anhydrous organic compound in the liquid carbon dioxide or supercritical carbon dioxide to form anhydrous peracetic acid. The anhydrous organic compound may be selected from the group consisting of anhydrous ethanol, anhydrous acetaldehyde, and anhydrous acetic acid. In one embodiment, the anhydrous organic compound is acetic acid. In the embodiments with liquid carbon dioxide, the liquid carbon dioxide may be maintained at a pressure of between about 100 PSI and about 900 PSI. The liquid carbon dioxide having peracetic acid may be released to a pressure of about 75 PSI or less to form carbon dioxide snow having peracetic acid. The carbon dioxide snow may be compacted into dry ice wafers, cylinders, or bricks. In one embodiment, the anhydrous peracetic acid is present in the carbon dioxide at a concentration between about 0.05 mole % and about 15 mole %.

Another embodiment of the invention provides a system for forming an anhydrous sterilant having a first reaction vessel containing a liquid selected from at least one of anhydrous ethanol, anhydrous acetaldehyde, and anhydrous acetic acid, an ozone source in fluid communication with the first reaction vessel to oxidizing the liquid to peracetic acid, and a pump for pumping liquid from the first reaction vessel to a second reaction vessel, wherein the second reaction vessel contains carbon dioxide. The system may also include a sparger in fluid communication with the ozone source for diffusing ozone into the liquid in the first reaction vessel, a first pressure release valve connected to the first reaction vessel, a second pressure release valve connected to the second reaction vessel, and an ozone destruct unit connected in fluid communication with the first pressure release valve.

Another embodiment of the invention provides a system for forming an anhydrous sterilant having a reaction vessel in fluid communication with a liquid carbon dioxside source, a liquid source in fluid communication with the reaction vessel. The liquid source may contain at least one of anhydrous ethanol, anhydrous acetaldehyde, and anhydrous acetic acid, an ozone source, and a carbon dioxide gas source. The ozone source and carbon dioxide source may be in fluid communication with the reaction vessel. The system may also include a sparger in fluid communication with the ozone source for diffusing ozone into the liquid in the reaction vessel, a pressure release valve connected to the reaction vessel, an ozone destruct unit connected in fluid communication with the pressure release valve, and a pump for pumping liquid from the liquid source into the reaction vessel.

Another embodiment of the invention provides for anhydrous sterilant composition, having anhydrous peracetic acid dissolved in, suspended in, or adsorbed to carbon dioxide. The carbon dioxide may be in a liquid, solid, or supercritical state. In one embodiment, the carbon dioxide is in the liquid state, and the anhydrous peracetic acid may be present in the liquid carbon dioxide at a concentration between about 0.05 mole % and about 15 mole %. In another embodiment, the concentration is between about 1 mole % and about 10 mole %. In another embodiment, the carbon dioxide may be in the solid state, and the anhydrous peracetic acid may be present in the solid carbon dioxide at a concentration between about 0.05 mole % and about 15 mole %. In another embodiment, the concentration is between about 1 mole % and about 10 mole %. In another embodiment, the anhydrous peracetic acid may be adsorbed to the solid carbon dioxide.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
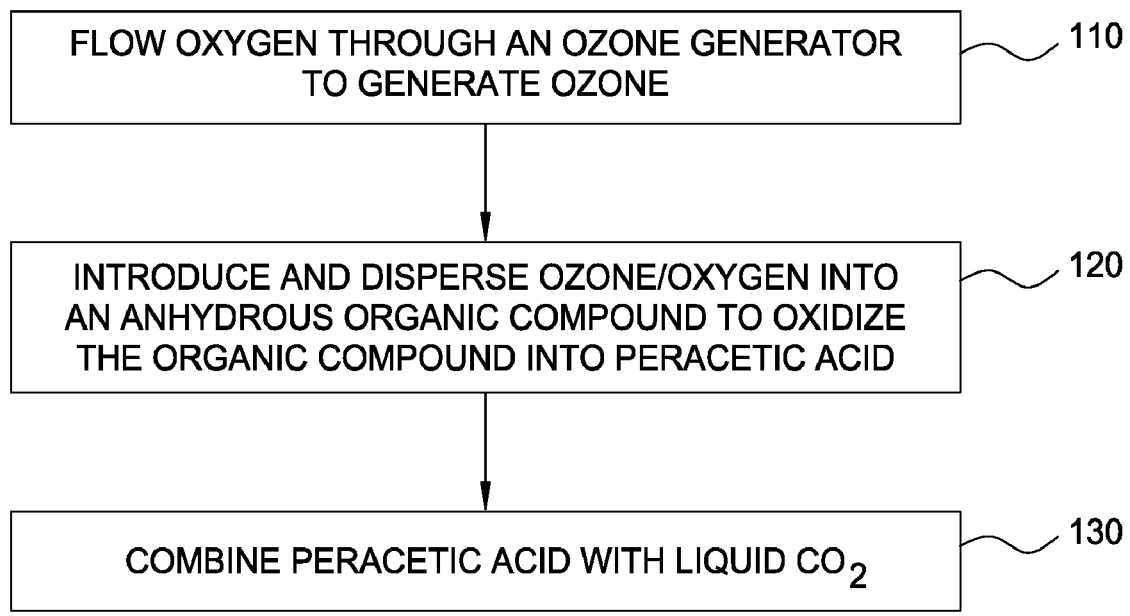
FIG. 1 is a flow chart of a process for forming an anhydrous sterilant, according to one embodiment of the invention.

FIG. 1 illustrates a flow chart of a process 100 for forming an anhydrous sterilant, according to one embodiment of the invention. In step 110, ozone is generated in a flow of concentrated oxygen gas. In step 120, the ozone/oxygen mixture is dispersed into an anhydrous liquid organic compound to oxidize the anhydrous organic compound into anhydrous peracetic acid. Several compounds may oxidize into peracetic acid, including ethanol, acetaldehyde, and acetic acid. Additionally, some ketones, such as acetone, yield formic and acetic acid upon ozonolysis, and the acetic acid may then be oxidized further by ozone to peracetic acid. In one embodiment, the liquid organic compound may be acetic acid. The reaction of acetic acid with ozone forms an equilibrium of acetic acid, ozone, peracetic acid and oxygen as indicated below:

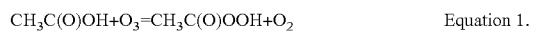

CH$_3$C(O)OH+O$_3$=CH$_3$C(O)OOH+O$_2$     Equation 1.

In step 130, the peracetic acid equilibrium mixture may be combined with carbon dioxide. In one embodiment, the equilibrium mixture is pumped into liquid carbon dioxide, and the combination of equilibrium mixture and liquid carbon dioxide may be used in a desired process as an anhydrous sterilant to treat surfaces. In another embodiment the equilibrium mixture may be combined with supercritical carbon dioxide and the combination of equilibrium mixture and supercritical carbon dioxide may be used in a desired process as an anhydrous sterilant to treat surfaces. In another embodiment, after pumping the peracetic acid equilibrium mixture in to the liquid carbon dioxide, the combination of equilibrium mixture and liquid carbon dioxide may be converted from the liquid form into dry ice or dry ice snow to form solid carbon dioxide with anti-microbial properties. Alternatively, the per- acetic acid containing equilibrium mixture is combined with dry ice snow and mixed to form carbon dioxide snow with anti-microbial properties. In either case, the snow may be compressed into dry ice wafers, cylinders, or bricks for transportation, storage, and use.

Figure 2:
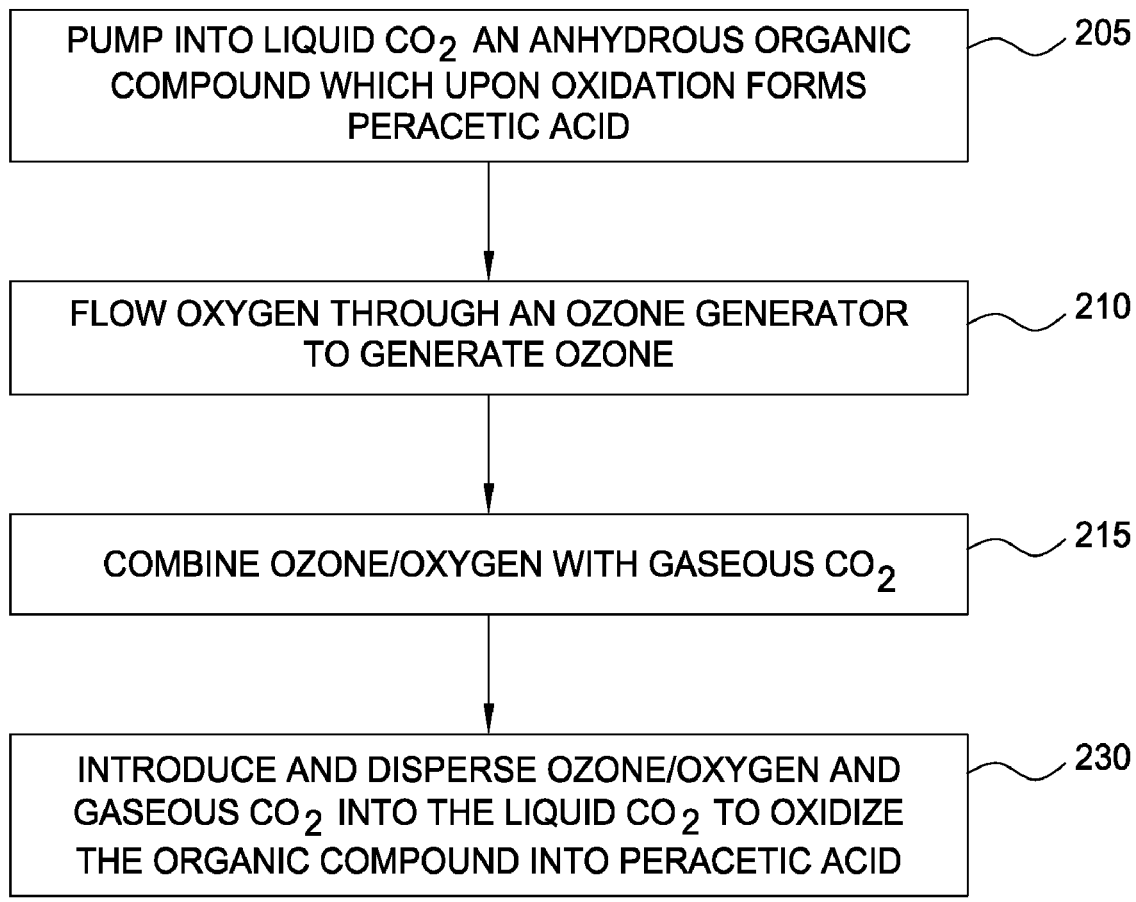
FIG. 2 is a flow chart of a process for forming an anhydrous sterilant, according to one embodiment of the invention.

FIG. 2 illustrates a flow chart of a process 200 for forming an anhydrous sterilant, according to one embodiment of the invention. In step 205 an anhydrous liquid organic compound is pumped into liquid carbon dioxide. In step 210, an ozone feedstock is generated in a flow of concentrated oxygen gas. The ozone feedstock is pressurized with a flow of carbon dioxide gas in step 215 to form an ozone/air/carbon dioxide gas mixture. In step 230 the gas mixture is introduced in to the liquid carbon dioxide and the anhydrous liquid organic compound to oxidize the anhydrous liquid organic compound into peracetic acid. The peracetic acid loaded liquid carbon dioxide may be used in a desired process as an anhydrous sterilant to treat surfaces. In another embodiment the peracetic acid loaded liquid carbon dioxide may be converted from the liquid form into dry ice or dry ice snow to form a solid carbon dioxide with anti-microbial properties. The snow may be compressed into dry ice wafers, cylinders, or bricks for transportation, storage, and use.

Figure 3:
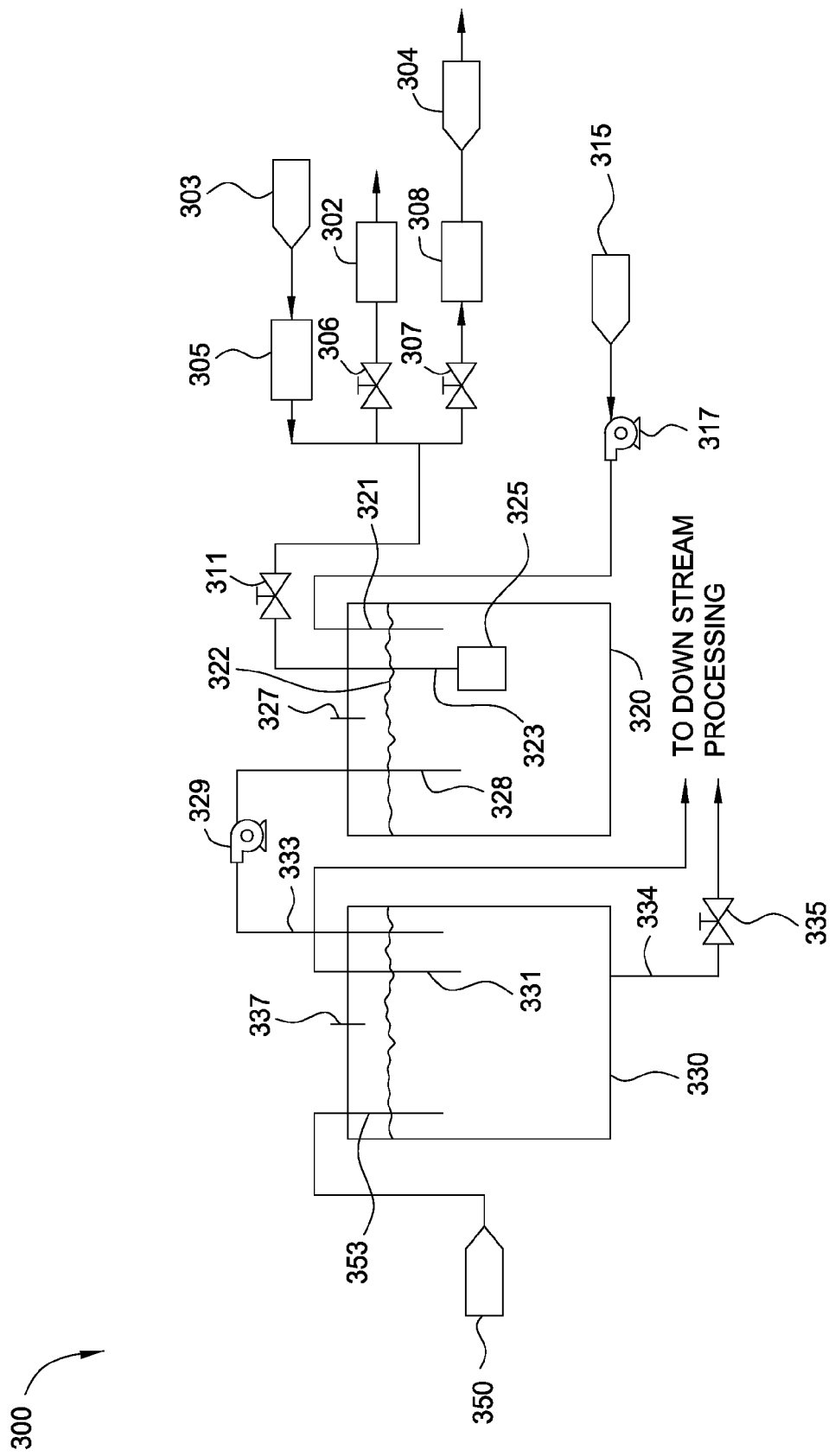
FIG. 3 is a process flow diagram for a processing unit for the formation of an anhydrous sterilant, according to one embodiment of the invention.

FIG. 3 illustrates a process flow diagram of a processing unit 300 for the formation of an anhydrous sterilant, according to one embodiment of the invention. Oxygen source 303 provides and oxygen feed stock to an ozone generator 305. The oxygen flow rate may have a value between about 100 ml/min. and about 10000 ml/min., preferably, between about 250 ml/min. and about 750 ml/min., more preferably, between about 300 ml/min. to about 600 ml/min. The oxygen feed stock may be concentrated to include above about 90% v/v oxygen, preferably, above 93% v/v oxygen, and more preferably, above 95% v/v. The ozone may be formed by passing the concentrated oxygen feed through the ozone generator 305, such as the Ozonia CFS-2 generator. The oxygen feed may be analyzed for ozone content by first passing the oxygen feed through valve 307 and into ozone analyzer 308, such as the In-USA H1-X high concentration ozone feed gas analyzer. The resulting concentration of ozone in the oxygen feed may be between about 1% v/v and about 15% v/v. In one embodiment, the ozone concentration may be about 10% v/v. The oxygen feed gas may be passed from ozone analyzer 308 to an ozone destruct unit 304 to reduce ozone to oxygen before the oxygen feed gas enters the atmosphere. If excess ozone is generated, a valve 306 may be opened and the ozone flowed to another ozone destruct unit 302 for destruction.

With valves 306 and 307 closed, the oxygen feed exiting ozone generator 305 may pass through valve 311 and through dip-tube 323 extending to the bottom of reaction vessel 320. Dip-tube 323 may be terminated by a sparger 325. Because the tubing, valves, connections, and fittings are used to transport ozone, the tubing, valves, connections, and fittings may be constructed with materials that are compatible with ozone, and does not corrode or deteriorate when in contact with ozone. In one embodiment the tubing, valves, connections, and fittings are made of 316-stainless steel. In one embodiment, sparger 325 is made of 304-stainless steel, and in another embodiment made of 316-stainless steel. The reaction vessels 320 and 330 may also be constructed with materials that are compatible with ozone, and does not corrode or deteriorate when in contact with ozone. In one embodiment the reaction vessels 320 and 330 are made of 316-stainless steel.

Sparger 325 promotes the formation of oxygen feed gas bubbles in the anhydrous liquid organic compound contained within reaction vessel 320. In one embodiment the anhydrous liquid organic compound may be acetic acid. The anhydrous acetic acid may be maintained at a level 322. The anhydrous acetic acid may be pumped by a pump 317 from an anhydrous acetic acid source 315, through dip-tube 321, and into reaction vessel 320. The ozone reacts with the anhydrous acetic acid as described above in respect to step 120 of FIG. 1. Excess pressure buildup may escape through pressure release valve 327. The gas escaping through pressure release valve 327 may pass through an ozone destruct unit (not shown) in order to eliminate any potential unreacted ozone in the gas mixture.

The equilibrium mixture of anhydrous acetic acid, ozone, peracetic acid and oxygen may be pumped by pump 329 through dip-tube 333 into a pressurized reaction vessel 330. The pressurized reaction vessel 330 contains liquid carbon dioxide supplied to the pressurized reaction vessel 330 from carbon dioxide source 350 through dip-tube 353. The liquid carbon dioxide may have a temperature between about −70° F. (the triple point temperature) and about 88° F. (the critical temperature), preferably, between about 0° F. and about 80° F. The liquid carbon dioxide may be maintained at a pressure between about 75 PSI (the triple point pressure) and about 1072 PSI (the critical pressure), preferably, between about 100 PSI and about 900 PSI. In one embodiment the liquid carbon dioxide may be maintained at a pressure of about 800 PSI at room temperature (about 68° F.). In another embodiment the liquid carbon dioxide may be maintained at a pressure of about 300 PSI at about 0° F. Pressurized reaction vessel 330 may include a stirrer (not shown) to stir the liquid carbon dioxide and the equilibrium mixture of anhydrous acetic acid, ozone, peracetic acid, and oxygen. Excess pressure buildup may escape through pressure release valve 337. The resulting solution of peracetic acid in liquid carbon dioxide may have a peracetic acid concentration of between about 0.05 mole % and about 15 mole %, preferably, between about 1 mole % and 10 mole %. Peracetic acid loaded liquid carbon dioxide may be pumped from the pressurized reaction vessel 330 via dip-tube 331 or let out by gravity through tube 334 and valve 335 for downstream processing. The peracetic acid loaded liquid carbon dioxide may be used in a desired process as an anhydrous sterilant to treat surfaces. In another embodiment the peracetic acid loaded liquid carbon dioxide may be converted from the liquid form into dry ice or dry ice snow to form a solid carbon dioxide with anti-microbial properties. The dry ice may be formed by releasing the pressurized liquid carbon dioxide from the pressurized reaction vessel 330 via dip-tube 331 or through tube 334 and valve 335. The expansion of the liquid and the evaporation of carbon dioxide gas cools the carbon dioxide to its freezing point, whereupon the carbon dioxide turns into a solid. The snow may be compressed into dry ice wafers, cylinders, or bricks for transportation, storage, and use.

In another embodiment the equilibrium mixture of anhydrous acetic acid, ozone, peracetic acid, and oxygen may be introduced into the pressurized reaction vessel 330 containing supercritical carbon dioxide. By supercritical carbon dioxide is meant carbon dioxide at or above its critical pressure (Pc) and critical temperature (Tc). In one embodiment the operating conditions for the supercritical carbon dioxide may be between about 88° F. and about 120° F., preferably, between about 90° F. and about 95° F., and between about 1072 PSI and about 1740 PSI, preferably, between about 1100 PSI and about 1450 PSI. The peracetic acid loaded supercritical carbon dioxide may be used in a desired process as an anhydrous sterilant to treat surfaces.

In an alternative embodiment, the equilibrium mixture of anhydrous acetic acid, ozone, peracetic acid and oxygen may be pumped from reaction vessel 320 and combined directly with dry ice snow to form a solid carbon dioxide with pearcetic acid adsorbed to it, resulting in dry ice snow with anti-microbial properties. The antiseptic dry ice snow may be compressed into dry ice wafers, cylinders, or bricks for transportation, storage, and use.

Figure 4:
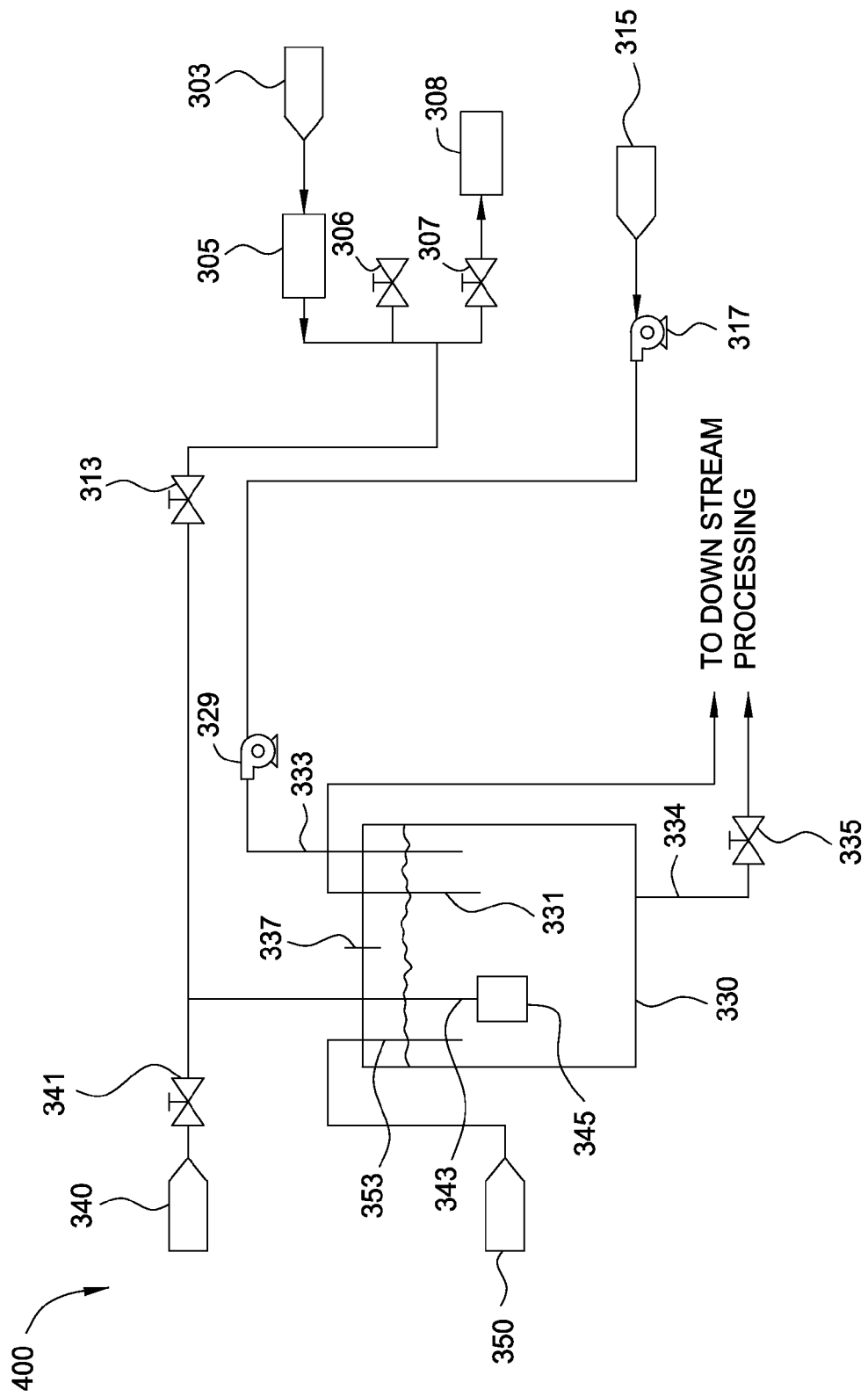
FIG. 4 is a process flow diagram for a processing unit for the formation of an anhydrous sterilant, according to one embodiment of the invention.

FIG. 4 illustrates a process diagram of a processing unit 400 for the formation of an anhydrous sterilant, according to another embodiment of the invention. In this embodiment, anhydrous acetic acid may be blended with the liquid carbon dioxide in reaction vessel 330, as described above in respect to step 205 of FIG. 2. The anhydrous acetic acid may be pumped directly from anhydrous acetic acid source 315 into reaction vessel 330. Valve 313 may then be opened and the oxygen feed exiting ozone generator 305 may be combined with a pressurizing carbon dioxide gas flowing from carbon dioxide source 340 through valve 341. The combined gases, having a total pressure above the pressure in the pressurized reaction vessel 330, may then flow into the pressurized reaction vessel 330 through dip-tube 343 and sparger 345. The ozone reacts with the anhydrous acetic acid as described above in respect to step 230 of FIG. 2. The gas escaping through pressure release valve 337 may pass through an ozone destruct unit (not shown) in order to eliminate any potential unreacted ozone in the gas mixture.

Peracetic acid loaded liquid carbon dioxide may be pumped from the pressurized reaction vessel 330 via dip-tube 331 or let out by gravity through tube 334 and valve 335 for downstream processing. The peracetic acid loaded liquid carbon dioxide may be used in a desired process as an anhydrous sterilant to treat surfaces. In another embodiment the peracetic acid loaded liquid carbon dioxide may be converted from the liquid form into dry ice or dry ice snow to form a solid carbon dioxide with anti-microbial properties. The snow may be compressed into dry ice wafers, cylinders, or bricks for transportation, storage, and use.

Figure 5:
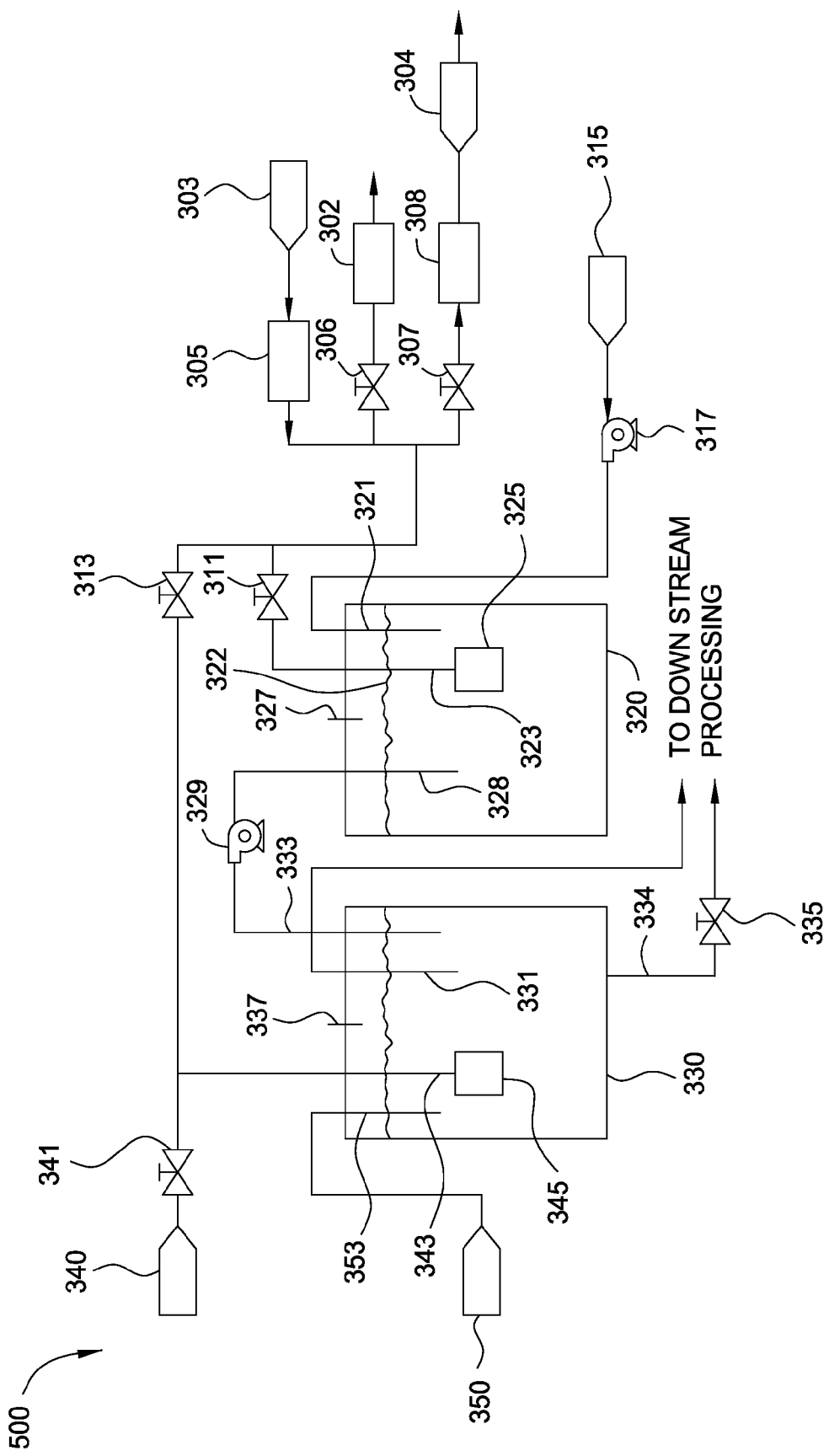
FIG. 5 is a process flow diagram for a processing unit for the formation of an anhydrous sterilant, according to one embodiment of the invention.

FIG. 5 illustrates a process diagram of a processing unit 500 for the formation of an anhydrous sterilant, according to another embodiment of the invention. This embodiment combines the processing units 300 and 400 into one processing unit 500 which may alternatively function to operate according to process 100 or process 200. By keeping valve 313 closed and valve 311 open, the processing unit 500 may function as processing unit 300. Alternatively, by keeping valve 313 open and valve 311 closed, the processing unit 500 may function as processing unit 400. In another embodiment, both valves 311 and 313 may be open. In this embodiment the ozone oxidizes the anhydrous acetic acid in reaction vessel 320, and further promotes the oxidation equilibrium of Equation 1 to maintain or increase the concentration of peracetic acid in reaction vessel 330. Peracetic acid loaded liquid carbon dioxide or supercritical carbon dioxide may be used as a disinfectant of surfaces. In one embodiment, the peracetic acid loaded carbon dioxide is sprayed onto the surface of an object in need of disinfection. The peracetic acid loaded carbon dioxide may be applied for the disinfection of medical supplies and to prevent bio film formation in pulp industries. It may be applied during water purification as a disinfectant and for plumming disinfection. The peracetic acid loaded carbon dioxide may be suitable for cooling tower water disinfection, as it effectively prevents bio film formation and controls Legionella bacteria. The peracetic acid loaded carbon dioxide may also be used as a disinfectant as a part of a cooling step in a processes where cooling is needed. Because the peracetic acid loaded carbon dioxide is anhydrous, there may not be a need to provide drying to remove water from the objects being disinfected. Peracetic acid loaded dry ice may be used when packaging and shipping of materials which may require an antiseptic environment, such as foodstuffs and biomedical materials. As the dry ice sublimes, peracetic acid is released to provide a dry, antiseptic environment around the packaged material.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. An anhydrous sterilant composition, comprising:
   a) anhydrous peracetic acid dissolved in, suspended in, or adsorbed to carbon dioxide, wherein the carbon dioxide is in a solid state.

2. The composition of claim 1, wherein the anhydrous peracetic acid is present in the solid carbon dioxide at a concentration between about 0.05 mole % and about 15 mole %.

3. The composition of claim 2, wherein the concentration is between about 1 mole % and about 10 mole %.

4. The composition of claim 1, wherein the anhydrous peracetic acid is adsorbed to the solid carbon dioxide.

* * * * *